United States Patent
Cuero Rengifo et al.

(10) Patent No.: US 9,890,201 B2
(45) Date of Patent: Feb. 13, 2018

(54) BIOLOGICAL DEVICES AND METHODS OF USE THEREOF FOR THE STUDY AND CONTROL OF ALZHEIMER'S DISEASE

(71) Applicants: INTERNATIONAL PARK OF CREATIVITY, Bogota (CO); Rengifo Raul Cuero, Cypress, TX (US); Diana Marcela Vasquez Forero, Bucaramanga (CO)

(72) Inventors: Raul Cuero Rengifo, Cypress, TX (US); Diana Marcela Vasquez Forero, Bucaramanga (CO)

(73) Assignee: International Park of Creativity, Bogota (CO)

( * ) Notice: Subject to any disclaimer, the term of this patent is extended or adjusted under 35 U.S.C. 154(b) by 102 days.

(21) Appl. No.: 14/909,174

(22) PCT Filed: Aug. 4, 2014

(86) PCT No.: PCT/US2014/049574
§ 371 (c)(1),
(2) Date: Sep. 8, 2016

(87) PCT Pub. No.: WO2015/017852
PCT Pub. Date: Feb. 5, 2015

(65) Prior Publication Data
US 2016/0168214 A1 Jun. 16, 2016

Related U.S. Application Data

(60) Provisional application No. 61/861,474, filed on Aug. 2, 2013.

(51) Int. Cl.
*C12N 1/15* (2006.01)
*C07K 14/47* (2006.01)
*C07K 14/245* (2006.01)

(52) U.S. Cl.
CPC ........ *C07K 14/4711* (2013.01); *C07K 14/245* (2013.01)

(58) Field of Classification Search
None
See application file for complete search history.

(56) References Cited

U.S. PATENT DOCUMENTS

2003/0077261 A1 4/2003 Paris et al.

FOREIGN PATENT DOCUMENTS

WO 2012012739 1/2012
WO 2012145459 10/2012

OTHER PUBLICATIONS

Braselmann et al., Trends Biochem Sci. (2013) vol. 38, pp. 337-344.*
International Search Report and Written Opinion for PCT/US2014/049574 dated Dec. 11, 2014.
Dahms et al. "Metal binding dictates conformation and function of the amyloid precursor protein (APP) E2 domain" 2012, J. Mol. Biol, 416:438-452.
Kaserer et al., "Insight from TonB hybrid proteins into the mechanism of iron transport through the outer membrane," 2008, J. Bacteriol, 190:2001-4016.
Noinaj et al. "TonB-dependent transporters: regulation, structure, and function," 2010, Ann. Rev. Microbiol., 2010, 64:43-60.
Vodovar et al., "Complete genome sequence of the entomopathogenic and metabolically versatile soil bacterium *Pseudomonas entomophila*," Nature Biotech., 2006, 24:673-679.

* cited by examiner

*Primary Examiner* — James S Ketter
(74) *Attorney, Agent, or Firm* — Gardner Groff Greenwald & Villanueva, PC (57) ABSTRACT

Described herein are devices and methods for simultaneously expressing amyloid precursor protein and TonB protein. For example, the biological devices and methods described herein increase the production of these two proteins while also reducing the cost, making these proteins more widely accessible for medical research purposes, including for the development of diagnostic tests for Alzheimer's disease. The amyloid precursor protein and TonB protein produced by the devices and methods described herein, as well as the devices themselves, can be used in experiments designed to model the interactions between metals and β-amyloid that are characteristic of Alzheimer's disease.

21 Claims, 6 Drawing Sheets

SEQUENCE LISTING

<160> NUMBER OF SEQ ID NOS: 4

<210> SEQ ID NO 1

```
<211> LENGTH: 2372
<212> TYPE: DNA
<213> ORGANISM: Artificial sequence
<220> FEATURE:
<223> OTHER INFORMATION: Synthetic construct

<400> SEQUENCE: 1
tagaactagt ggattacccc cgggctgcag gaattcgata tcaaaatgct gcccggtttg      60
gcactgctcc tgctggccgc ctggacggct cgggcgctgg aggtacccac tgatggtaat     120
gctggcctgc tggctgaacc ccagattgcc atgttctgtg gcagactgaa catgcacatg     180
aatgtccaga tgggaagtg ggattcagat ccatcaggga ccaaaacctg cattgatacc     240
aaggaaggca tcctgcagta ttgccaagaa gtctaccctg aactgcagat caccaatgtg     300
gtagaagcca accaaccagt gaccatccag aactggtgca agcggggccg caagcagtgc     360
aagacccatc cccactttgt gattccctac cgctgcttag ttggtgagtt tgtaagtgat     420
gcccttctcg ttcctgacaa gtgcaaattc ttacaccagg agaggatgga tgtttgcgaa     480
actcatcttc actggcacac cgtcgccaaa gagacatgca gtgagaagag taccaacttg     540
catgactacg gcatgttgct gccctgcgga attgacaagt ccgaggggt agagtttgtg      600
tgttgcccac tggctgaaga aagtgacaat gtggattctg ctgatgcgga ggaggatgac     660
tcggatgtct ggtggggcgg agcagacaca gactatgcag atgggagtga agacaaagta     720
gtagaagtag cagaggagga agaagtggct gaggtggaag aagaagaagc cgatgatgac     780
gaggacgatg aggatggtga tgaggtagag aagaggctg aggaacccta cgaagaagcc      840
acagagagaa ccaccagcat tgccaccacc accaccacca ccacagagtc tgtggaagag     900
gtggttcgag aggtgtgctc tgaacaagcc gagacggggc cgtgccgagc aatgatctcc     960
cgctggtact tgatgtgac tgaagggaag tgtgccccat tcttttacgg cggatgtggc    1020
ggcaaccgga caactttga cacagaagag tactgcatgg ccgtgtgtgg cagcgccatg    1080
tcccaaagtt tactcaagac tacccaggaa cctcttgccc gagatcctgt aaacttcct    1140
acaacagcag ccagtacccc tgatgccgtt gacaagtatc tcgagacacc tggggatgag    1200
aatgaacatg cccattttcca gaaagccaaa gagaggcttg aggccaagca ccgagagaga    1260
atgtcccagg tcatgagaga atgggaagag gcagaacgtc aagcaaagaa cttgcctaaa    1320
gctgataaga aggcagttat ccagcatttc caggagaaag tggaatcttt ggaacaggaa    1380
gcagccaacg agagacagca gctggtggag acacacatgg ccagagtgga agccatgctc    1440
aatgaccgcc gccgcctggc cctggagaac tacatcaccg ctctgcaggc tgttcctcct    1500
cggcctcgtc acgtgttcaa tatgctaaag aagtatgtcc gcgcagaaca gaaggacaga    1560
cagcacaccc taaagcattt cgagcatgtg cgcatggtgg atcccaagaa agccgctcag    1620
atccggtccc aggttatgac acacctccgt gtgatttatg agcgcatgaa tcagtctctc    1680
tccctgctct acaacgtgcc tgcagtggcc gaggagattc aggatgaagt tgatgagctg    1740
cttcagaaag agcaaaacta ttcagatgac gtcttggcca acatgattag tgaaccaagg    1800
atcagttacg gaaacgatgc tctcatgcca tctttgaccg aaacgaaaac caccgtggag    1860
ctccttcccg tgaatggaga gttcagcctg gacgatctcc agccgtggca ttcttttggg    1920
gctgactctg tgccagccaa cacagaaaac gaagttgagc ctgttgatgc ccgccctgct    1980
gccgaccgag gactgaccac tcgaccaggt tctgggttga caaatatcaa gacgcgaggag    2040
atctctgaag tgaagatgga tgcagaattc cgacatgact caggatatga agttcatcat    2100
caaaaattgg tgttctttgc agaagatgtg ggttcaaaca aaggtgcaat cattggactc    2160
```

```
atggtgggcg gtgttgtcat agcgacagtg atcgtcatca ccttggtgat gctgaagaag    2220
aaacagtaca catccattca tcatggtgtg gtggaggttg acgccgctgt caccccagag    2280
gagcgccacc tgtccaagat gcagcagaac ggctacgaaa tccaaccta caagttcttt     2340 gagcagatgc agaactgaaa gcttatcgat ac                                  2372

<210> SEQ ID NO 2
<211> LENGTH: 1391
<212> TYPE: DNA
<213> ORGANISM: Artificial Sequence
<220> FEATURE:
<223> OTHER INFORMATION: Synthetic construct

<400> SEQUENCE: 2
gggatctcga ggaattctca ctggaacagc gcgtcactcg acaggccatt cttctccaga      60
atctcccgca ggcgcttcag cgcctcgacc tggatctgac gaacccgctc gcgggtcagg     120
ccgatttcct ggccgacctc ttccagcgtg ctgctttcgt gaccgcgcaa gccgaagcgg     180
cgaatcacca cctcacgctg cttgtcggtg agttccgtca gctgctttcg ctgagatcgt     240
catcctgcag cagctcgcac ggatcggtgg ggcgatcgtc ggtgagcgta tccagcaggg     300
tcttgtccga gtccggacca agagagacgt ctaccgaagt cacccgttcg ttcaggccga     360
gcatgcgctt gacctcggcg accggcttct ccagcaggtt ggcgatttct tcgggtgaag     420
gttcgtggtc gagcttgtgg gtcagttccc gcgccgcacg caggtagacg ttgagctcct     480
tgaccacatg gatcggcaag cgaatggtcc gggtctggtt catgatggcc cgctcgatgg     540
tctggcggat ccaccaggtg gcgtaggtcg agaaccggaa tccgcgctcc ggatcgaact     600
tctccacggc gcggatcagg cctaggttgc cttcctcgat caggtcgagc agggacagtc     660
cgcgattgac atagcgccgg gcgatcttca ccaccaaccg caggttgctc tcgatcatcc     720
gcttccgacc agcgggatcg cccttctgcg ccagacgagc gaagtggact tcctcttcgg     780
gcgtcaacag gggcgagaaa ccgatttcgt tgagatacag ctgcgttgcg tccaacgcgc     840
gcgtgtagtc gatgtgcttg tgttgtttgg aagagaagga agtggtggct tttggagttg     900
cccggggaga aggctgctcg tcggcagacg actcgtccag catgatgccg gctccagga     960 ggagcacttc atcatcgtgg tcaaactccg gcccttcttt tttgagtgcc atgtcgttat    1020
cccttgcatg agttcgactc aagcccgggc gattcctttc ccgctggaca cgcccggacc    1080
cgctcaccta catgatgtgg gcgggcgaac tcccggtcag cgacgtggca aatattgcag    1140
tggatcgaca ggcttaccct ggcggcgaat ctcgaagtgc agcttcaccc gatcggttcc    1200
tgtggagccc atctcggcaa tcgattgccc taccttgacc tgttgccctt cccgcaccag    1260
cagcctgcgg ttgtgaccgt aggcactcac gtaggtctcg ttgtgtttga tgatgaccaa    1320
ctcgccgtag ccccgcaaac cactaccggc gtatacaacg gtcccaccag acgcagccag    1380
gtaccaagct t                                                         1391

<210> SEQ ID NO 3
<211> LENGTH: 747
<212> TYPE: DNA
<213> ORGANISM: Artificial Sequence
<220> FEATURE:
<223> OTHER INFORMATION: Synthetic construct

<400> SEQUENCE: 3
gaattcatga cgaaaacgcg ctcgaacatg gcgcgctacg gcaccagcct ggccatcgtg      60
```

-continued

```
ctgggcgtgc acgtggtcgc cgtggtgctg acgctcaact ggtcggtgcc ccaggccatc      120
gagctgccgc cggcagcgat gatggtcgag ttggcgccgt tgccggagcc cgcgccaccg      180
ccaccgccca aggccgcgcc caagccaccg gcagaggtcg aggagccgcc gctgcccaag      240
ctggtggagg cccccaagcc gaagatcgcc atcgccaagc cgcccaagcc caaggccaag      300
ccgcagccgc ccaagcctga gaaaaagcct gagccgccga aggacgaacc accggccaag      360
gacgatgtgg cggataccc gccaagcaac gcgcagccgc agaaatcggc cgcaccggca      420
ccgagcatcg cctccaacag caatgccctg cccagctggc agagcgacct gctgcgccac      480
ctggccaagt acaagaagta cccggaagac gctcgccgtc gcggcctgca gggcatcaac      540
cgcctgcgct tcgtggtcga cgccgagggc aaggtagtct cgtactcgct ggccggaggc      600
tcgggcagcg cggcgctgga ccgggcgacc ctggaaatga tccgtcgcgc aggctccgta      660
ccgaagccgc cagcggagct gttgaacaat ggcacgatcg aagtcgtggc gccgttcgtc      720
tattccctgg accgacgctg aggatcc                                         747

<210> SEQ ID NO 4
<211> LENGTH: 890
<212> TYPE: DNA
<213> ORGANISM: Artificial Sequence
<220> FEATURE:
<223> OTHER INFORMATION: Synthetic construct

<400> SEQUENCE: 4
ggattcaaag aggagaaata ctagatggtg agcaagggcg aggagctgtt caccggggtg       60
gtgcccatcc tggtcgagct ggacggcgac gtaaacggcc acaagttcag cgtgtccggc      120
gagggcgagg gcgatgccac ctacggcaag ctgaccctga agttcatctg caccaccggc      180
aagctgcccg tgcccctggcc caccctcgtg accaccttcg gctacggcct gcaatgcttc      240
gcccgctacc ccgaccacat gaagctgcac gacttcttca gtccgccat gcccgaaggc      300 tacgtccagg agcgcaccat cttcttcaag gacgacggca actacaagac ccgcgccgag      360
gtgaagttcg agggcgacac cctggtgaac cgcatcgagc tgaagggcat cgacttcaag      420
gaggacggca acatcctggg gcacaagctg gagtacaact acaacagcca caacgtctat      480
atcatggccg acaagcagaa gaacggcatc aaggtgaact tcaagatccg ccacaacatc      540
gaggacggca gcgtgcagct cgccgaccac taccagcaga cacccccat cggcgacggc      600 cccgtgctgc tgcccgacaa ccactacctg agctaccagt ccgccctgag caaagacccc      660
aacgagaagc gcgatcacat ggtcctgctg gagttcgtga ccgccgccgg gatcactctc      720
ggcatggacg agctgtacaa gtaataatac tagagccagg catcaaataa aacgaaaggc      780
tcagtcgaaa gactgggcct ttcgttttat ctgttgtttg tcggtgaacg ctctctacta      840
gagtcacact ggctcacctt cgggtgggcc tttctgcgtt tataaagctt                 890
```

BIOLOGICAL DEVICES AND METHODS OF USE THEREOF FOR THE STUDY AND CONTROL OF ALZHEIMER'S DISEASE

CROSS REFERENCE TO RELATED APPLICATION

This application claims priority upon U.S. Provisional Application Ser. No. 61/861,474, filed Aug. 2, 2013. The application is hereby incorporated by reference in its entirety for all of its teachings.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

The term "dementia" describes a set of symptoms that can include loss of memory, mood changes, and problems with communication and reasoning. Alzheimer's disease is the most common form of dementia and affects more than 26 million people worldwide. Incidence of Alzheimer's disease is expected to increase as the world's population ages; currently, there is no cure for this disease.

The causes of Alzheimer's disease are not well-understood, though abnormal structures called plaques and tangles have been identified in the brains of deceased Alzheimer's patients. Plaques are deposits of a protein fragment called $\beta$-amyloid, whereas tangles are twisted fibers of a different protein (tau) that accumulates inside cells. Some reports have indicated that Alzheimer's disease is associated with a high concentration of metals in the brain.

Due to the difficulty of accessing cerebral tissue in a living organism, progress in the study and understanding of Alzheimer's disease has been slow. While various Alzheimer's-associated proteins are commercially available, the cost of acquiring significant amounts of them for further research is prohibitive. A need thus exists for a method for producing proteins associated with Alzheimer's disease cheaply and efficiently. A further need exists for a model system for studying the interaction of $\beta$-amyloid and metals in cell culture and/or in a living organism. Additionally, a definitive diagnosis of Alzheimer's disease can only be made through autopsy after death. Therefore, a need exists for earlier diagnosis of Alzheimer's disease so that intervention can be administered to slow the progress of the disease or to mitigate Alzheimer's symptoms. This application addresses those needs.

SUMMARY

Described herein are devices and methods for simultaneously expressing amyloid precursor protein and TonB protein. For example, the biological devices and methods described herein increase the production of these two proteins while also reducing the cost, making these proteins more widely accessible for medical research purposes, including for the development of diagnostic tests for Alzheimer's disease. The amyloid precursor protein and TonB protein produced by the devices and methods described herein, as well as the devices themselves, can be used in experiments designed to model the interactions between metals and $\beta$-amyloid that are characteristic of Alzheimer's disease.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "an isolated nucleic acid" includes mixtures of two or more such nucleic acids, and the like.

"Optional" or "optionally" means that the subsequently described event or circumstance can or cannot occur, and that the description includes instances where the event or circumstance occurs and instances where it does not. For example, the phrase "optionally includes a gene for a selective marker" means that the gene may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed that while specific reference of each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules A, B, and C are disclosed as well as a class of molecules D, E, and F, and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, If a variety of additional steps can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Heterologous" genes and proteins are genes and proteins that have been experimentally put into a cell that are not normally expressed by that cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, particle bombardment, and exposure to a magnetic field. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells may be made competent using procedures known in the art. Exemplary procedures for producing competent cells are provided in the Examples.

I. DNA Constructs and Biological Devices

The biological devices described herein can be used to express amyloid precursor protein and TonB protein at high levels in culture media. In one aspect, the biological device can increase the production of amyloid precursor protein and TonB protein. The device is generally composed of host cells, where the host cells are transformed with a DNA construct described herein that promotes the expression of amyloid precursor protein and TonB protein in microbial cells or in culture media.

It is understood that one way to define the variants and derivatives of the genetic components and DNA constructs described herein is through defining the variants and derivatives in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed by published algorithms (see Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of conservative mutations and homology can be combined together in any combination, such as embodiments that have at least 70%, 75%, 80%, 85%, 90%, 95%, or 99% homology to a particular sequence wherein the variants are conservative mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, the DNA construct described herein can promote the expression of proteins such as, for example, amyloid precursor protein and TonB protein, from bacteria. In one aspect, the DNA construct is from 5' to 3' the following genetic components in the following order: (a) a gene that expresses amyloid precursor protein and (b) a gene that expresses TonB protein.

In one aspect, the gene that expresses amyloid precursor protein is isolated from mammals. In one aspect, the mammals are primates. In a further aspect, the primates are humans, gorillas, chimpanzees, or gibbons. In another aspect, the primates are New World monkeys such as *Callithrix jacchus* or strepsirrhine primates such as *Otolemur garnetti*. In another aspect, the mammals are horses, rhinoceroses, orcas, pigs, or giant pandas. In a further aspect, the gene that expresses amyloid precursor protein in the DNA construct has SEQ ID NO. 1 or a derivative or variant thereof.

In another aspect, the gene that expresses TonB protein is isolated from bacteria. In a further aspect, the bacteria are *Pseudomonas entomophila*, *P. putida*, *P. syringae*, *P. fluorescens*, *P. resinovorans*, or another *Pseudomonas* species or strain. In a further aspect, the gene that expresses TonB protein in the DNA construct has SEQ ID NO. 3 or a derivative or variant thereof.

In another aspect, the DNA construct further includes (c) a promoter, (d) a terminator or stop sequence, (e) a gene that confers resistance to an antibiotic (a "selective marker"), (f) a reporter protein, (g) a riboswitch, or a combination thereof.

In a further aspect, the DNA construct is from 5' to 3' the following genetic components in the following order: (1) a promoter, (2) a gene that expresses amyloid precursor protein, (3) a gene that expresses TonB protein, and (4) a terminator or stop sequence.

In one aspect, a regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter may also be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, Fe promoter, and GAL1 promoter. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides away from a ribosomal binding site. In one aspect, the promoter is a T7 promoter.

In a further aspect, the riboswitch in the DNA construct comprises SEQ ID NO. 2 or a derivative or variant thereof.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an "intrinsic terminator" is a sequence wherein a hairpin structure can form in the nascent transcript and wherein the hairpin disrupts the mRNA/DNA/RNA polymerase complex. As used herein, a "Rho-dependent" transcription terminator requires a Rho factor protein complex to disrupt the mRNA/DNA/RNA polymerase complex.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In another aspect, the DNA construct comprises the following components in the following sequence: a gene that expresses amyloid precursor protein having SEQ ID NO. 1, a riboswitch having SEQ ID NO. 2, and a gene that expresses TonB protein having SEQ ID NO. 3.

In certain aspects, the DNA construct can include a gene that expresses a reporter protein. The selection of the reporter protein can vary. For example, the reporter protein can be a yellow fluorescent protein, red fluorescent protein, a green fluorescent protein, or a cyan fluorescent protein. In one aspect, the gene that expresses the reporter protein has SEQ ID NO. 4. The amount of fluorescence that is produced by the biological device can be correlated to the amount of DNA incorporated into the microbial cells. The fluorescence produced by the device can be detected and quantified using techniques known in the art. For example, spectrofluorometers are typically used to measure fluorescence. The Examples provide exemplary procedures for measuring the amount of fluorescence as a result of the expression of DNA.

The DNA construct described herein can be part of a vector. In one aspect, the vector is a plasmid, a phagemid, a cosmid, a yeast artificial chromosome, a bacterial artificial chromosome, a virus, a phage, or a transposon.

In general, plasmid vectors containing replicon and control sequences that are derived from species compatible with the host cell are used in connection with these hosts. Vectors capable of high levels of expression of recombinant genes and proteins are well known in the art. The vector ordinarily carries a replication origin as well as marking sequences that are capable of providing phenotypic selection in transformed cells. Plasmid vectors useful for the transformation of a variety of host cells are well known and are commercially available. Such vectors include, but are not limited to, pWLNEO, pSV2CAT, pOG44, PXT1, pSG (Stratagene), pSVK3, pBSK, pBR322, pYES, pYES2, pBSKII, and pUC vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the ordinarily skilled artisan to select host cells that have been successfully transfected with the plasmids (for example, by culturing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector that confers antibiotic resistance can survive. Optionally, only cells containing the vector to be expressed will be cultured, as this will result in the highest production efficiency of the desired gene products (e.g., amyloid precursor protein and TonB protein). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BsaBI, NotI, XhoI, SphI, SbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g. amount of DNA needed, precise volumes of reagents, purification techniques, as well as information about salt concentration, pH, optimum temperature, incubation time, and the like) are made available by commercial enzyme suppliers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', often starting just after a promoter, the order and direction of elements inserted into a plasmid is especially important. If a plasmid is to be simultaneously digested with multiple restriction enzymes, these enzymes must be compatible in terms of buffer, salt concentration, and other incubation parameters.

In some aspects, prior to ligation using a ligase enzyme and/or electromagnetic ligation techniques, a plasmid that has been digested with a restriction enzyme is treated with an alkaline phosphatase enzyme to remove 5' terminal phosphate groups. This prevents self-ligation of the plasmid and thus facilitates ligation of heterologous nucleic acid fragments into the plasmid.

In one aspect, the nucleic acids (e.g., genes that express amyloid precursor protein and TonB protein) used in the DNA constructs described herein can be amplified using the polymerase chain reaction (PCR) prior to being ligated into a plasmid or other vector. Typically, PCR-amplification techniques make use of primers or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the ordinarily skilled practitioner with primer design. Primers can optionally incorporate restriction enzyme recognition sites at their 5' ends to assist in later ligation into plasmids or other vectors.

PCR can be carried out using purified DNA, unpurified DNA that has been integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. Alternatively, electromagnetic amplification techniques can be used. PCR products can be purified by techniques known in the art such as, for example, gel electrophoresis followed by extraction from the gel using commercial kits and reagents.

In a further aspect, the vector can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of the coding sequence.

As used herein, "expression" refers to transcription and/or accumulation of an mRNA derived from a gene or DNA fragment. Expression may also be used to refer to translation of mRNA into a peptide, polypeptide, or protein.

Exemplary methods for producing the DNA constructs described herein are provided in the Examples. Restriction enzymes and purification techniques known in the art can be used to prepare the DNA constructs. After the vector incorporating the DNA construct has been produced, it can be incorporated into host cells using the methods described below.

II. Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce amyloid precursor protein and TonB protein.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which exogenous nucleic acid is transferred or introduced into the host cell. A transformed cell includes the primary subject cell and its progeny. The host cells can be naturally-occurring cells or "recombinant" cells. Recombinant cells are distinguishable from naturally-occurring cells in that naturally-occurring cells do not contain heterologous nucleic acid sequences introduced using molecular biology techniques. In one aspect, the host cell is a prokaryotic cell, such as, for example, *E. coli*. In other aspects, the host cell is yeast such as, for example, *Saccharomyces cerevisiae*. Host cells transformed with the DNA construct described herein are referred to as biological devices.

The DNA construct is first delivered into the host cell. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the cell membrane through which the vector containing the DNA construct enters. Still another method involves exposing the cells to be transformed to a minicurrent electromagnetic field. Exemplary procedures for transforming yeast and bacteria with specific DNA are provided in the Examples. In certain aspects, two or more types of DNA can be incorporated into the host cells. Thus, different proteins can be produced from the same bacteria at enhanced rates.

Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. A variety of other carbon sources are contemplated, including, but not limited to: monosaccharides such as glucose and fructose, disaccharides such as lactose and sucrose, oligosaccharides, polysaccharides such as starch, and mixtures thereof. Unpurified mixtures extracted from feedstocks are also contemplated and can include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Furthermore, the use of different media results in different growth rates and different stationary phase densities. Protein production is highest when cells are in stationary phase. A rich media results in a short doubling time and higher cell density at stationary phase. Minimal media results in slow growth and low final cell densities. Efficient agitation and aeration increase final cell densities. A skilled artisan will be able to determine which type of media is best suited to culture a particular species and/or strain of host cell.

Culturing or fermenting of host cells may be accomplished by any technique known in the art. In one aspect, batch fermentation can be conducted. In batch fermentation, the composition of the culture medium is set at the beginning of culturing and the system is closed to future artificial alterations. In some aspects, a limited form of batch fermentation can be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation can be carried out on any scale and may include methods in which literal "fermentation" is carried out as well as other culture methods that are non-fermentative.

III. Methods for Increasing the Production of Amyloid Precursor Protein and TonB Protein from Microbial Cells Once the microbial cells have been transformed with the DNA construct described herein, the cells can be cultured in a suitable medium. The choice of a culture medium will depend on the number and type of host cells and an ordinary practitioner will be capable of selecting a culture medium suitable for the cells being grown.

Once the biological devices have been cultured for a sufficient time to produce the desired proteins (e.g., amyloid precursor protein and TonB protein), the proteins are isolated. In one aspect, the proteins are purified from the media containing the biological devices using a technique known in the art such as, for example, extraction, precipitation, ultracentrifugation, size exclusion chromatography, ion exchange chromatography, affinity chromatography, high-pressure liquid chromatography, electrophoresis, any other technique known in the art, or a combination thereof. In a further aspect, the microbial cells must be lysed to release the proteins of interest. In an alternative aspect, the microbial cells secrete the proteins of interest into the culture medium.

In one aspect, the biological devices are cultured in the presence of one or more metals or metal salts to produce amyloid precursor protein and TonB protein. In one aspect, the metal can be iron, copper, or zinc. In another aspect, the metal is a single metal. In an alternative aspect, the metal is a mixture of two or more metals. In a still further aspect, the metals can be introduced to solutions containing the proteins of interest as elemental metals or as metal salts. In this aspect, the metal salts can be sulfate salts or chloride salts. In a further aspect, the metals can be present at concentrations of from 0.1 mM to 100 mM, or from 0.5 mM to 50 mM, or from 1 mM to 10 mM, or 2 mM.

In one aspect, a method for expressing amyloid precursor protein and TonB protein involves
(a) culturing the biological devices described herein; and
(b) removing the proteins of interest.

In one aspect, the amyloid precursor protein and/or TonB protein produced from a microbial cell can be used in medical research applications. In this aspect, the amyloid precursor protein and the TonB protein produced using the biological devices described herein are cheaper and/or more cost effective than other commercially-available sources of these same proteins. In this aspect, the metals can be elemental metals or can be ions. In a further aspect, the metal can be iron, copper, or zinc. In another aspect, the metal is a single metal. In an alternative aspect, the metal is a mixture of two or more metals. In a still further aspect, the metals can be introduced to solutions containing the proteins of interest as elemental metals or as metal salts. In this aspect, the metal salts can be sulfate salts or chloride salts. In a further aspect, the metals can be present at concentrations of from 0.1 mM to 100 mM, or from 0.5 mM to 50 mM, or from 1 mM to 10 mM, or 2 mM.

In another aspect, the amyloid precursor protein, TonB protein, and/or biological devices described herein can be useful in conducting research into the pathology, pathogenesis, and/or treatment of diseases associated with β-amyloid plaques such as, for example, Alzheimer's disease, Lewy body dementia, inclusion body myositis, and cerebral amyloid angiopathy. In a further aspect, the interaction of amyloid precursor protein, amyloid beta, and or amyloid plaques with metals can be assessed. In this aspect, the metals can be elemental metals or can be ions. In a further aspect, the metal can be iron, copper, or zinc. In another aspect, the metal is a single metal. In an alternative aspect, the metal is a mixture of two or more metals. In a still further aspect, the metals can be introduced to solutions containing the proteins of interest as elemental metals or as metal salts. In this aspect, the metal salts can be sulfate salts or chloride salts. In a further aspect, the metals can be present at concentrations of from 0.1 mM to 100 mM, or from 0.5 mM to 50 mM, or from 1 mM to 10 mM, or 2 mM.

In one aspect, when metals are added to the culture medium containing the biological devices, the biological devices can be allowed to grow and form colonies. In this aspect, the growth of the biological devices containing the DNA construct described herein can be compared to the growth of cells not containing such a construct. In a further aspect, the growth and behavior of the biological devices can serve as proxies or models for the interaction of metals and amyloid precursor protein, amyloid beta, and/or amyloid plaques, since performing similar experiments in living tissues can be difficult.

In one aspect, biological devices such as those described herein are used as models for in vivo behavior of amyloid precursor protein. In this aspect, without wishing to be bound by theory, the TonB protein expressed by the biological devices provides energy for transporting metals, metal complexes, and or other large products across cell membranes, or acts as an ion channel for metals and metal complexes.

In a further aspect, biological devices such as those described herein are used in diagnostic tests for the detection of Alzheimer's disease in living patients, including early stages of the disease. In this aspect, the use of these diagnostic tests can identify Alzheimer's patients at an early stage, when few or no symptoms are present, thus enabling physicians and caregivers to start treatment early and delay the progression of the disease. In a still further aspect, the biological devices are used in diagnostic tests for other amyloid-plaque-associated diseases such as, for example, Lewy body dementia, inclusion body myositis, and cerebral amyloid angiopathy.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such processes and conditions.

Preparation of DNA Construct

The DNA construct was composed of genetic components described herein and assembled in plasmid vectors (e.g., pBSKII). Sequences of genes and/or proteins with desired properties were identified in GenBank; these included an amyloid precursor protein gene and a TonB gene. These sequences were synthesized by CloneTex Systems, Inc. (Austin, Tex.). Other genetic parts were also obtained for inclusion in the DNA constructs including, for example, promoter genes (e.g. T7 promoter), reporter genes (e.g. yellow fluorescent reporter protein), terminator sequences, and regulatory sequences (e.g. riboswitch). These genetic parts included restriction sites for ease of insertion into plasmid vectors.

Figure 2:
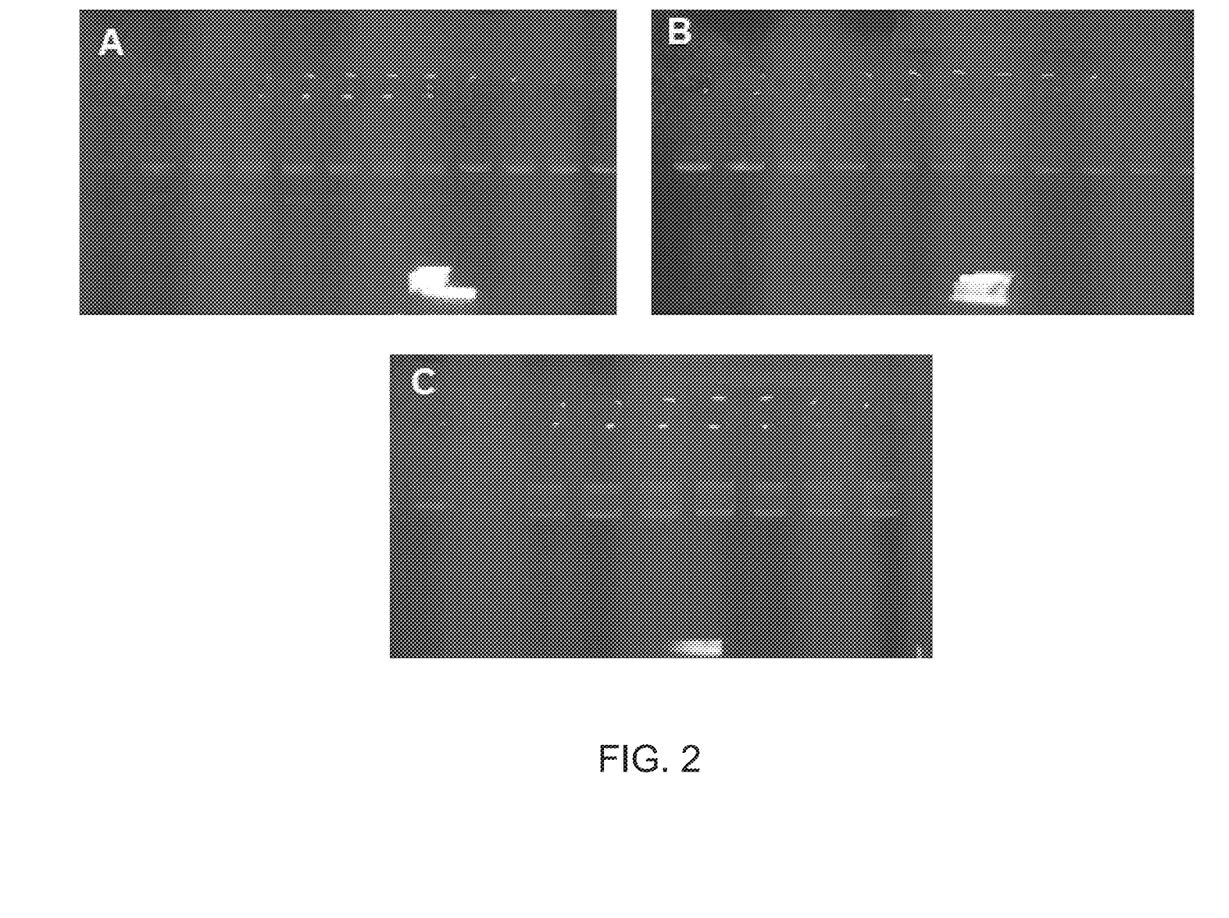
FIG. 2 shows images of electrophoresis gels of individual genetic parts used to synthesize the DNA construct described herein. (A) TonB gene; (B) riboswitch, (C) yellow fluorescent reporter gene.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were excised from the plasmids in which they were provided using restriction enzymes. The excised fragments were purified by agarose gel electrophoresis (see FIG. 2) prior to ligation. Equal proportions of the riboswitch gene, the TonB gene, and the yellow fluorescent reporter gene were mixed.

A pBSKII plasmid already containing a gene for the amyloid precursor protein was then digested with HindIII restriction enzyme according to directions and using reagents provided by the enzyme's supplier (Promega). The complete insert, containing HindIII restriction sites on each end, was then ligated into the plasmid. A ratio of 3 parts backbone vector to 4 parts insert mixture was used for ligation. T4 DNA ligase, ligase buffer (supplied by Promega), and nuclease-free water were added to the mixture of vector and insert. The reaction mixture was placed into an electromagnetic chamber and subjected to a minicurrent (900 mA) magnetic field with a strength of 0.35 Gauss. Successful construction of the insert and ligation of the insert into the plasmid were confirmed by gel electrophoresis.

Figure 1:
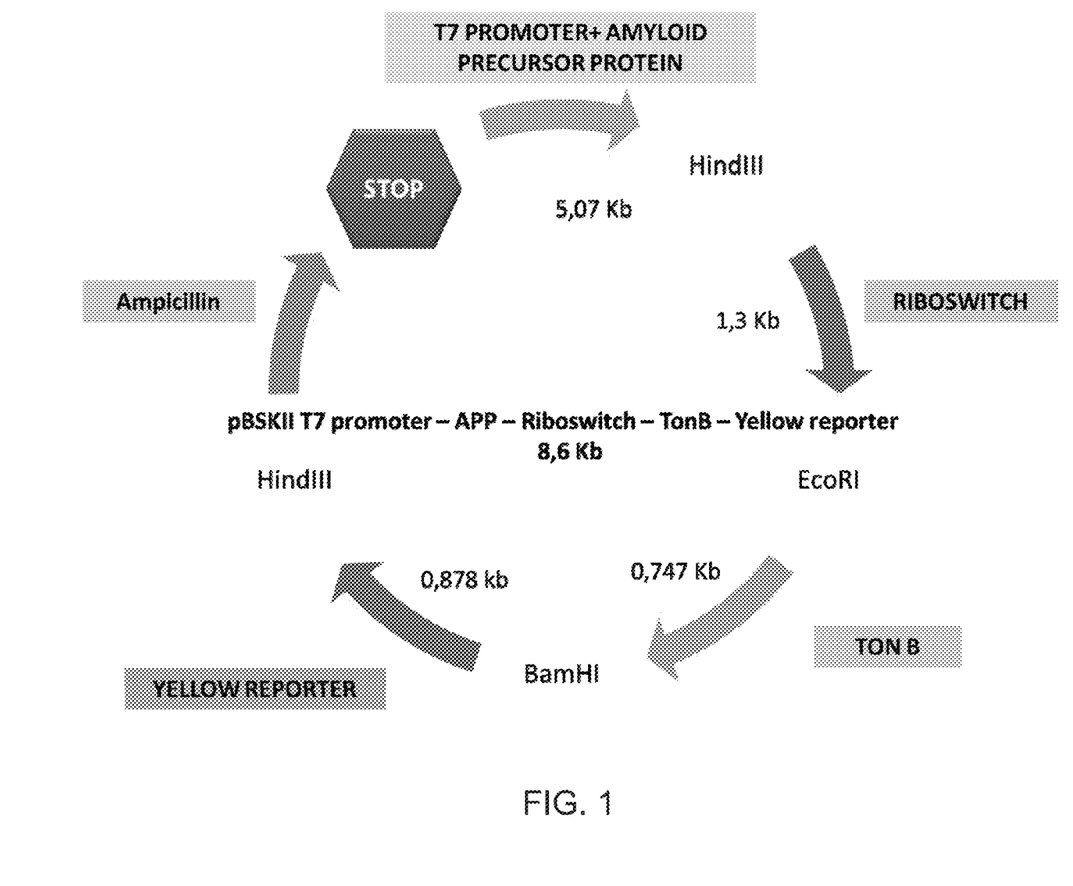
FIG. 1 shows a DNA construct, described herein, incorporated in a plasmid.

A schematic of the DNA construct is depicted in FIG. 1. From 5' to 3', the construct includes T7 promoter, a gene expressing amyloid precursor protein, a riboswitch, a gene expressing TonB protein, a yellow fluorescent reporter protein, a terminator or stop sequence, and a selective marker for ampicillin resistance. The DNA construct was incorporated into a pBSKII plasmid.

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis. 1989. Molecular cloning: A Laboratory Manual, 2nd ed., vol. 1. Cold Spring Harbor Laboratory Press, Cold Spring Harbor, N.Y.). Digestion and ligation were used to ensure assembly of DNA synthesized parts using restriction enzymes and reagents (PCR master mix, restriction enzymes: EcoRI, BamHI and HindIII, alkaline phosphatase and quick ligation kit, all from Promega). DNA was quantified using a NanoVue spectrophotometer (GE Life Sciences) and a standard UV/visible spectrophotometer using the ratio of absorbances at 260 nm versus 280 nm. In order to verify final ligations, DNA was visualized and purified via electrophoresis using a Thermo EC-150 power supply.

The DNA construct was made with gene parts having sequence sizes ranging from 747 to 1300 bp, including gene parts fundamental for expression of such as, for example, a riboswitch, a promoter, a reporter gene, and transcriptional terminators or stops. Backbone plasmids and synthetic inserts can be mixed together for ligation purposes at different ratios. In one aspect, the ratio of backbone plasmid to synthetic insert is 3:4. After the vector comprising the DNA construct has been produced, the resulting vector can be incorporated into the host cells using the methods described below.

Figure 3:
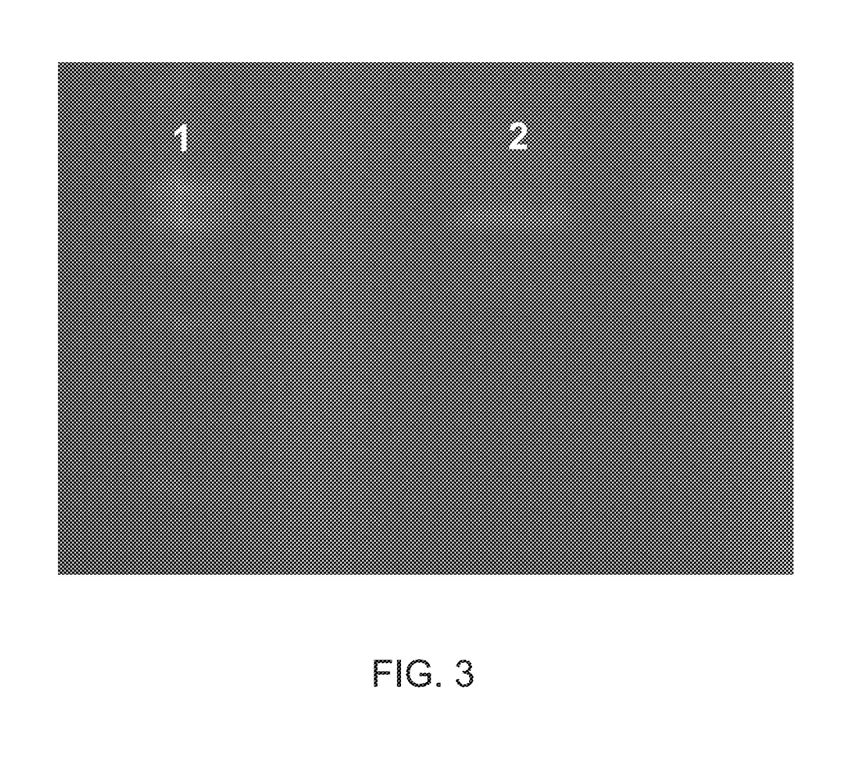
FIG. 3 shows an image of an electrophoresis gel of the complete DNA construct described herein. Lane 1: 1 kb molecular weight marker. Lane 2: DNA construct.
Figure 4:
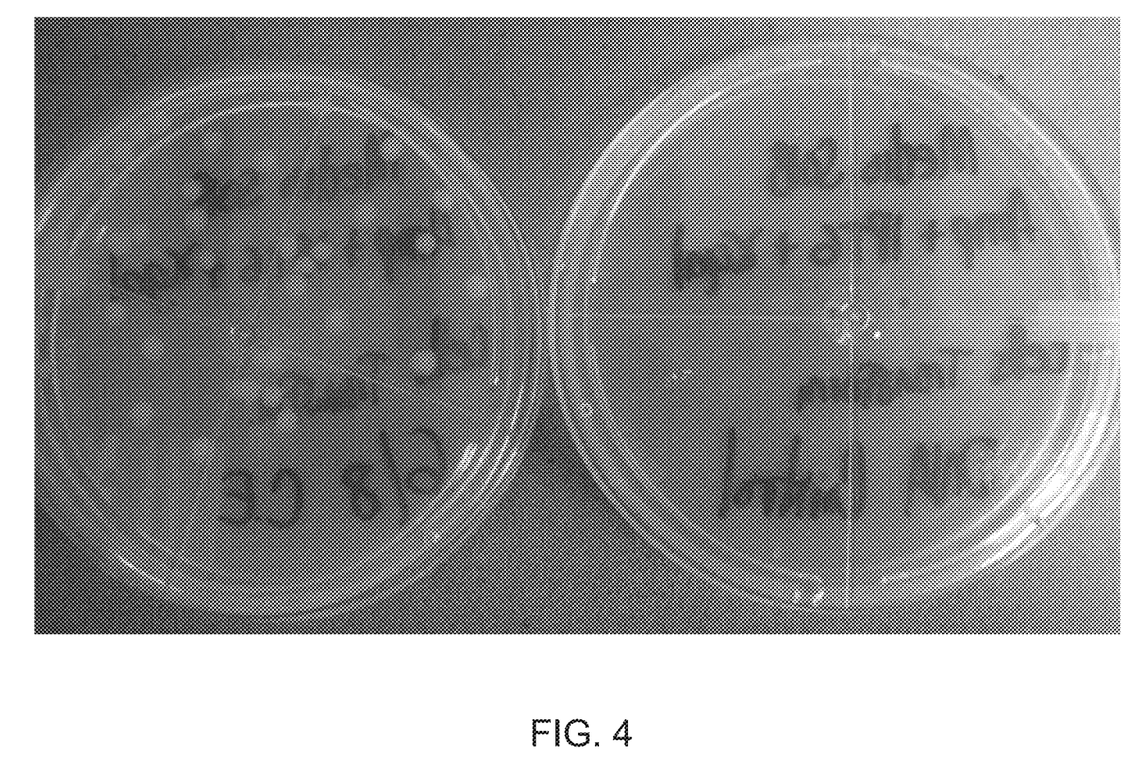
FIG. 4 shows plates of transformed cells (left) and an untransformed control (right). The plating media contained ampicillin. The DNA constructs used to transform the cells included an ampicillin resistance gene.

The DNA device was constructed by assembling a plasmid (pBSKII) having the genetic components in the following order: (1) a gene that expresses amyloid precursor protein (SEQ ID NO. 1; T7 promoter and amyloid precursor protein together are 5070 bp), (2) a riboswitch (SEQ ID NO. 2, 1300 bp), and (3) a gene that expresses TonB protein (SEQ ID NO. 3, 747 bp). In certain embodiments, the reporter protein (SEQ ID NO. 4, 878 bp) that produces fluorescence can be incorporated into the plasmid prior to the terminator from the 5' to 3' direction. The amount of fluorescence correlates to protein production in media. The DNA construct was transformed into cells, as described below, to produce the biological devices. A plasmid containing the DNA construct is shown in FIG. 1. A gel of the successfully-ligated DNA construct is shown in FIG. 3.

Host Cell Purification and Transformation

Top 10 Chemically Competent E. coli cells from Life Technologies were transformed with the DNA construct described herein using a modified version of a protocol provided by the supplier. 25 µL of cells were mixed with 5 µL of the DNA construct. Cells were placed on ice for 20 mM Cells were then subjected to heat shock for 50 seconds at 42° C. After heat shock, cells were once again incubated on ice for 2 mM 250 µL of SOC medium (2% w/v tryptone, 0.5% w/v yeast extract, 8.56 mM NaCl, 2.5 mM KCl, 10 mM $MgCl_2$, 10 mM $MgSO_4$, 20 mM glucose) were added to the mixture of cells and inserts. The samples were placed in an electromagnetic chamber and subjected to a minicurrent (900 mA) that created a magnetic field of 0.35 Gauss for 15 minutes. After electromagnetic exposure, 100 µL aliquots were plated in petri dishes with SOB agar (same as SOC but without the glucose), ampicillin, isopropyl β-D-1-thiogalactopyranoside (IPTG), and 5-bromo-4-chloro-3-indolyl-β-D-galactopyranoside (X-gal). Petri dishes were then incubated for 18 hours.

DNA expression and effectiveness of transformation were determined by fluorescence of the transformed cells expressed in fluorescence units (FSUs), according a protocol provided by the manufacturer, using a 20/20 Luminometer (Promega). The blue fluorescence module (with a 450 nm excitation wavelength and a 600 nm emission wavelength) was used to evaluate the effectiveness of transformation. When no fluorescent reporter protein was assembled, no fluorescence was observed. Plasmid DNA extraction purification, PCR, and gel electrophoresis were also used to confirm transformation.

Protein Expression in Metal-Containing Media

Figure 5:
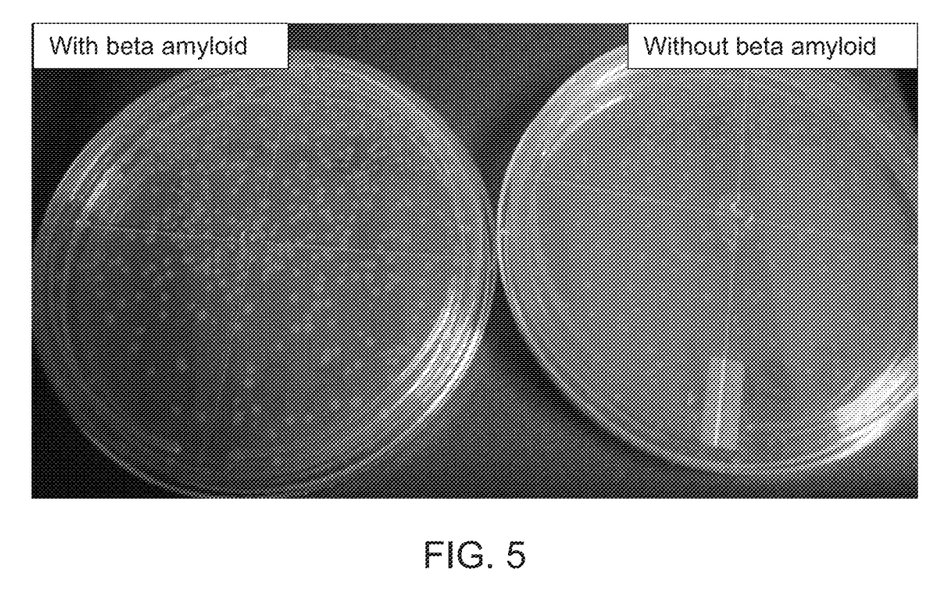
FIG. 5 shows growth of cells on media containing metals. Left: cells transformed with the DNA construct described herein. Right: untransformed cells.

The development of β-amyloid in the presence of metals was assessed. Transformed cells containing the DNA construct described herein were plated on 250 µL of agar with suitable media containing either 1 mM or 2 mM of iron metal, iron sulfate, copper chloride, or copper sulfate (i.e., 8 separate experiments). A positive control consisting of transformed cells that did not include a gene for the amyloid precursor protein was also assessed. Bacterial populations were assessed by counting colony forming units (CFUs). Results are presented in Table 1 and FIG. 5.

TABLE 1

CFU Count for Cells with and without DNA Construct Grown in Metal-Containing Media

| Metal (1 mM) | With DNA Construct | Without DNA Construct |
|---|---|---|
| Iron | $55 \times 10^6$ | $50 \times 10^6$ |
| Iron Sulfate | $79 \times 10^6$ | $70 \times 10^6$ |
| Copper Sulfate | $59 \times 10^6$ | $35 \times 10^6$ |
| Copper Chloride | $84 \times 10^6$ | $47 \times 10^6$ |
| None | $29 \times 10^6$ | $23 \times 10^6$ |

Thus, cells transformed with the DNA construct described herein are better able to survive in media containing metal ions.

Production and Quantification of β-Amyloid by ELISA

The alpha diagnostic beta amyloid 1-42 elisa kit was used to quantify protein production. The following procedure was used to produce β-amyloid.

1. Top 10 Chemically Competent *E. coli* cells transformed with the construct as depicted in FIG. 1 were inoculated into LB+ampicillin liquid medium, and then incubated at 37° C. for 7 hours. Growth of the cells was determined according the absorbance (optical density=OD), using spectrophotometer.
2. 10 mL sample of cells above were mixed with 150 mL of fresh LB+Ampicilin medium. In another experiment, 10 mL of sample of cells were mixed with 50 mL of fresh LB+Ampicilin medium.
3. Each cell culture was incubated at 37° C. for 4 hours.
4. After incubation, 100 μL of IPTCG was added to each sample.
5. Next, cell growth was determined according absorbance at 550-600 nm
6. Each culture was centrifuged at 5000 RPM for 15 minutes at room temperature, and a pellet was obtained.

The pellet from each experiment was subjected to an extraction process in order to isolate β-amyloid. The protein extraction was performed with the Open biotechnology protein extraction kit. The following procedure was used.

1. Resuspend the above obtained pellets-use 100 ml of lysis buffer for each 1 liter of the original culture.
2. Mix the pellet up into homogenous suspension and avoid bubble formation.
3. Add 1 ml of lysozyme per 1 liter of culture then vortex.
4. Completely lyse the cells, then freeze at −20° c.
5. Thaw the suspension in water bath at 37° c. The lysosyma is activated: the clearance or viscosity indicate lysis
6. Add 1 mL $CaCl_2$.
7. Add 1 mL of DNase.
8. Mix well and incubate at 37° C. for 5 min or until clear or the solution viscosity decreases. The extractant was left in a refrigerator 4° C.

Figure 6:
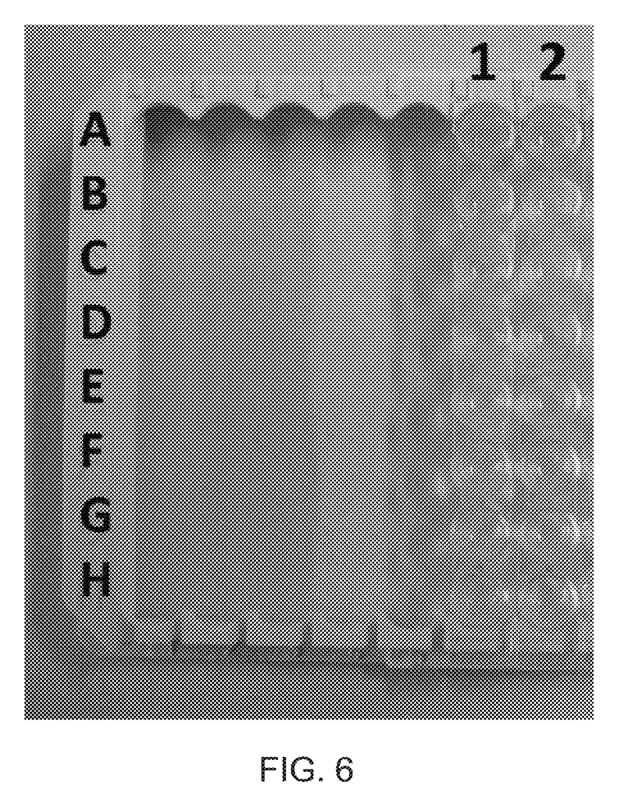
FIG. 6 shows extracted $\beta$-amyloid expressed from a device of the present invention as compared to standard $\beta$-amyloid using ELISA method.

FIG. 6 represents the ELISA Plate Wells (1-2 and corresponding assigned letter: A-H).

Blank (wells(G2, H1, H2)=dilution buffer without β-amyloid
Column 1=β-amyloid standard at different concentration
Column 2=β-amyloid samples from device FIG. 6 shows the different intensity of the color expressed by the different samples. This shows high intensity of color expressed by the bacterial device containing the β-amyloid protein. The high intensity as shown in D2, E2, and F2 compared to the standard correlates with higher concentration of the β-amyloid.

The corresponding concentration of β-amyloid in each well of FIG. 6 is shown in below in Table 2.

TABLE 2

Concentration of extracted β-amyloid from *E. Coli* transformed with genetic construct as compared to standard β-amyloid using ELISA method.

| Sample | | Concentration (pg/ml) |
|---|---|---|
| A1 | standard dilution 1:2 | 800 |
| B1 | standard dilution 1:4 | 400 |
| C1 | standard dilution 1:8 | 200 |
| D1 | standard dilution 1:16 | 100 |
| E1 | standard dilution 1:32 | 50 |
| F1 | standard dilution 1:64 | 25 |
| G1 | standard dilution 1:128 | 12.5 |
| H1 | Blank | 0 |
| A2 | sample 1 | 25 |
| B2 | sample 2 | 25 |
| C2 | sample 3 | 25 |
| D2 | sample 4 | 200 |
| E2 | sample 5 | 200 |
| F2 | sample 6 | 200 |
| G2 | Blank | 0 |
| H2 | Blank | 0 |

Table 2 shows different concentration of the extracted β-amyloid protein as compared to different concentrations of β-amyloid standards (A1, B1, C1, D1, E1, G1, G1). Blank (G1, G2, H2).
Blank=dilution buffer without β-amyloid
Column 1=β-amyloid standard at different concentrations
Column 2=β-amyloid samples from *E. Coli* transformed with genetic construct The results show higher concentration of β-amyloid in samples of bacterial device with higher volume of cells. Thus, the device when incubated in 150 mL showed higher concentration of β-amyloid (200 pg/ml) (D2, E2, and F2), while lower volumes of the device (50 mL)(A2, B2, and C2) produced lower concentration of β-amyloid production (25 pg/ml) (Table 2).

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A DNA construct comprising the following genetic components: (a) a gene that expresses amyloid precursor protein, wherein the gene is SEQ ID NO. 1 and (b) a gene that expresses TonB protein, wherein the gene is SEQ ID NO. 3.

2. The DNA construct of claim 1, further comprising a promoter.

3. The DNA construct of claim 2, wherein the promoter is a T7 promoter.

4. The construct of claim 1, further comprising a riboswitch.

5. The construct of claim 4, wherein the riboswitch has SEQ ID NO. 2.

6. The construct of claim 1, further comprising a terminator.

7. The construct of claim 1, wherein the construct further comprises a gene that confers resistance to an antibiotic.

8. The construct of claim 7, wherein the antibiotic comprises tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamycin, penicillin, or a combination thereof.

9. The construct of claim 1, wherein the construct further comprises a gene for a reporter protein.

10. The construct of claim 9, wherein the reporter protein comprises a red fluorescent protein, a cyan fluorescent protein, a green fluorescent protein, a yellow fluorescent protein, or a combination thereof.

11. The construct of claim 10 wherein the reporter protein has SEQ ID NO. 4.

12. The construct of claim 1, wherein the DNA construct comprises the following components from 5' to 3' in the following sequence: a gene that expresses amyloid precursor protein having SEQ ID NO. 1, a riboswitch having SEQ ID NO. 2, and a gene that expresses TonB protein having SEQ ID NO. 3.

13. A vector comprising the construct of claim 1.

14. The vector of claim 13, wherein the vector is a plasmid.

15. The vector of claim 13, wherein the vector is pWL-NEO, pSV2CAT, pOG44, PXT1, pSG (Stratagene) pSVK3, pBSK, pBR322, pYES, pYES2, pBSKII, or pUC.

16. The vector of claim 13, wherein the vector is pBSKII.

17. A biological device comprising host cells transformed with the vector of claim 14.

18. The device of claim 17, wherein the host cells comprise yeast or bacteria.

19. The device of claim 18, wherein the bacteria comprise *E. coli*.

20. The device of claim 17, wherein the host cells comprise yeast, and the vector is pYES2.

21. The device of claim 17, wherein the host cells comprise yeast, and the vector is pYES2 comprising (a) SEQ ID NO. 1, (b) SEQ ID NO. 3, and (c) a gene that expresses a fluorescent protein.

* * * * *